(12) United States Patent
Batchelor et al.

(10) Patent No.: US 11,986,358 B2
(45) Date of Patent: May 21, 2024

(54) SURGICAL PROTECTION SYSTEM

(71) Applicant: GYRUS ACMI, INC., Southborough, MA (US)

(72) Inventors: Kester J. Batchelor, Mound, MN (US); Huisun Wang, Maple Grove, MN (US); Theodore C. Blus, Arden Hills, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 598 days.

(21) Appl. No.: 16/365,898

(22) Filed: Mar. 27, 2019

(65) Prior Publication Data

US 2020/0306004 A1 Oct. 1, 2020

(51) Int. Cl.
*A61B 90/00* (2016.01)
*A61B 90/90* (2016.01)

(52) U.S. Cl.
CPC .............. *A61B 90/39* (2016.02); *A61B 90/04* (2016.02); *A61B 90/90* (2016.02); *A61B 90/03* (2016.02); *A61B 2090/0409* (2016.02); *A61B 2090/049* (2016.02); *A61B 2090/3908* (2016.02); *A61B 2090/395* (2016.02)

(58) Field of Classification Search
None
See application file for complete search history.

(56) References Cited

U.S. PATENT DOCUMENTS

| | | | |
|---|---|---|---|
| 5,827,269 A | 10/1998 | Saadat | |
| 6,173,199 B1 | 1/2001 | Gabriel | |
| 6,173,715 B1 * | 1/2001 | Sinanan | A61B 90/39 128/898 |
| 6,293,952 B1 | 9/2001 | Brosens et al. | |
| 6,338,709 B1 * | 1/2002 | Geoffrion | A61N 5/1002 600/3 |

(Continued)

FOREIGN PATENT DOCUMENTS

| | | |
|---|---|---|
| CN | 111743638 A | 10/2020 |
| EP | 2997926 A1 | 3/2016 |

(Continued)

OTHER PUBLICATIONS

"European Application Serial No. 20166421.6, Extended European Search Report dated Nov. 17, 2020", 13 pgs.

(Continued)

*Primary Examiner* — Katherine L Fernandez
*Assistant Examiner* — Farouk A Bruce
(74) *Attorney, Agent, or Firm* — Schwegman Lundberg & Woessner, P.A.

(57) ABSTRACT

A device comprising: (a) one or more markers, some or all of which are expandable rounded members that are expandable from a stored state to an expanded state and when in the expanded state each of the expandable rounded members expand to move into contact with a lumen in an organ; and (b) one or more tissue tags connected to the expandable rounded members or the expandable rounded members being made of a magnetized material; and wherein the expandable rounded members are configured to be located within and deployed from an insertion mechanism into the lumen in the organ.

13 Claims, 5 Drawing Sheets

(56) References Cited

U.S. PATENT DOCUMENTS

| | | | |
|---|---|---|---|
| 6,689,119 B1 * | 2/2004 | Di Caprio | A61M 25/0127 600/585 |
| 7,567,159 B2 | 7/2009 | Macken | |
| 8,510,012 B2 | 8/2013 | Amato et al. | |
| 8,670,816 B2 | 3/2014 | Green et al. | |
| 8,679,139 B2 | 3/2014 | Aguirre et al. | |
| 8,939,111 B2 | 1/2015 | Berntsen | |
| 9,320,539 B2 | 4/2016 | Daniel et al. | |
| 9,332,990 B2 | 5/2016 | Requarth | |
| 2001/0018594 A1 * | 8/2001 | Krag | A61B 17/32053 606/167 |
| 2004/0002626 A1 | 1/2004 | Feld et al. | |
| 2004/0010304 A1 * | 1/2004 | Weber | A61F 2/95 623/1.11 |
| 2004/0260273 A1 | 12/2004 | Wan | |
| 2005/0119734 A1 | 6/2005 | Spence et al. | |
| 2005/0119735 A1 * | 6/2005 | Spence | A61B 17/0401 623/2.36 |
| 2008/0097501 A1 | 4/2008 | Blier | |
| 2008/0114384 A1 * | 5/2008 | Chang | A61B 17/1114 606/153 |
| 2009/0124847 A1 * | 5/2009 | Doty | A61B 18/1442 606/50 |
| 2009/0221913 A1 | 9/2009 | Voegele et al. | |
| 2010/0094116 A1 | 4/2010 | Silverstein | |
| 2012/0101370 A1 | 4/2012 | Razzaque et al. | |
| 2012/0326875 A1 | 12/2012 | Coppola | |
| 2014/0046347 A1 | 2/2014 | Cully et al. | |
| 2015/0201944 A1 | 7/2015 | Starnes | |
| 2015/0238276 A1 | 8/2015 | Atarot et al. | |
| 2016/0106554 A1 | 4/2016 | Lavallee | |
| 2016/0166328 A1 * | 6/2016 | De Vries | A61B 90/30 600/7 |
| 2016/0166351 A1 | 6/2016 | Kleiner | |
| 2016/0220314 A1 | 8/2016 | Huelman et al. | |
| 2017/0224421 A1 | 8/2017 | Marczyk et al. | |
| 2019/0038178 A1 | 2/2019 | Sasaki et al. | |

FOREIGN PATENT DOCUMENTS

| | | |
|---|---|---|
| EP | 0853463 B1 | 5/2016 |
| EP | 3162294 A1 | 3/2017 |
| JP | 2016510672 | 4/2016 |
| WO | 1996/008999 A1 | 3/1996 |
| WO | 1998/035720 A2 | 8/1998 |
| WO | 1999/027839 A2 | 6/1999 |
| WO | 2001/008578 A1 | 2/2001 |
| WO | 2003/011394 A1 | 2/2003 |
| WO | 2011/021192 A1 | 2/2011 |
| WO | WO-2011100625 A2 | 8/2011 |
| WO | WO-2012045092 A2 | 4/2012 |
| WO | 2014/066042 A2 | 5/2014 |
| WO | 2014163990 | 10/2014 |
| WO | 2015/008248 A2 | 1/2015 |
| WO | 2015/138708 A1 | 9/2015 |
| WO | 2018/130956 A1 | 7/2018 |
| WO | 2019/010007 A1 | 1/2019 |

OTHER PUBLICATIONS

"European Application Serial No. 20166421.6, Partial European Search Report dated Aug. 3, 2020", 11 pgs.

"European Application Serial No. 20166421.6, Response filed Jun. 16, 2021 to Extended European Search Report dated Nov. 17, 2020", 8 pgs.

"European Application Serial No. 20166421.6, Communication Pursuant to Article 94(3) EPC dated Feb. 21, 2023", 4 pgs.

"European Application Serial No. 20166421.6, Response filed Jul. 20, 2023 to Communication Pursuant to Article 94(3) EPC dated Feb. 21, 2023", w claims, 6 pgs.

"Japanese Application Serial No. 2020-56138, Notification of Reasons for Refusal dated Aug. 14, 2023", w English Translation, 12 pgs.

"Chinese Application Serial No. 202010230940.5, Office Action dated Aug. 16, 2023", w English Translation, 22 pgs.

"Japanese Application Serial No. 2020-56138, Response filed Nov. 6, 2023 to Notification of Reasons for Refusal mailed Aug. 14, 2023", with English claims, 7 pgs.

"Chinese Application Serial No. 202010230940.5, Response filed Dec. 29, 2023 to Office Action mailed Aug. 16, 2023", with English claims, 11 pgs.

* cited by examiner

Fig-9

SURGICAL PROTECTION SYSTEM

FIELD

The present teachings relate to a surgical system that assists in marking a feature of interest so that the feature of interest can be avoided or regions around the feature of interest can be avoided. Specifically, the surgical protection system includes one or more markers, one or more tissue tags, one or more device tags, or a combination thereof that are deployable into a lumen and the markers, tissue effecting element, or both may include one or more tags (e.g., device tags or tissue tags) that are made of a magnetized material or include magnets to indicate a position of the markers or tags within the lumen.

BACKGROUND

Attempts have been made to move two or more surgical components away from each other during dissection of tissue to protect a location of interest from unintended contact with a surgical instrument. A catheter with a first polarity may be located in an organ or tissue and a tool including a first polarity may be used so that when the tool is moved towards the catheter the tool is moved away from the organ or tissue so that the organ or tissue is protected. Examples of some tools may be found in U.S. Pat. Nos. 5,827,269; 6,293,952; 7,567,159; and 9,320,539; U.S. Patent Application Publication No.: 2004/0002626; 2004/0260273; and 2008/0097501; and International Patent Application Publication No. WO2015/138708; WO2012/130956; and WO2019/010007 all of which are incorporated by reference herein in their entirety for all purposes.

It would be attractive to include a surgical device including one or more markers that are expandable to be located at a location of interest and preferably located within a lumen of an organ. What is needed is one or more markers that are made of a magnetized material or in include a magnetic so that the one or more markers mark a feature of interest or provide a target within a feature of interest and/or to protect the feature of interest. What is needed is a surgical system that includes one or more markers and one or more insertion mechanisms that deploy the locators into a predetermined location. It would be attractive to have a method of marking one or more features of interest or protecting a location proximate to a feature of interest.

SUMMARY

The disclosure meets one or more of the needs by providing: a device comprising: (a) one or more markers, some or all of which are expandable rounded members that are expandable from a stored state to an expanded state and when in the expanded state each of the expandable rounded members expand to move into contact with a lumen in an organ; and (b) one or more tissue tags connected to the expandable rounded members or the expandable rounded members being made of a magnetized material; and wherein the expandable rounded members are configured to be located within and deployed from an insertion mechanism into the lumen in the organ.

The present teachings provide. a surgical system comprising: one or more surgical devices including: (a) one or more tissue effecting elements; and (b) one or more markers; wherein when a tip of the one or more tissue effecting elements includes one or more device tags that are a magnetized material, the one or more markers include a tissue tag magnetic field sensor or when the one or more device tags in the tip of the one or more tissue effecting elements includes the tissue tag magnetic field sensor, the one or more markers include one or more tissue tags that are a magnetized material; and wherein: (i) a display system indicates a proximity of the tip of the one or more tissue effecting elements to the one or more markers; (ii) an alarm system provides a signal when the tip and the one or more markers are within a predetermined distance of each other; (iii) power supplied to the tip is removed when the tip and the one or more markers are within a predetermined distance of each other; or (iv) a combination thereof.

The teachings herein provide: a method comprising a method comprising: (a) deploying a set of one or more markers having one or more tissue tags into a lumen; and (b) inserting a tissue effecting element, having a tip with one or more device tags, into a same lumen with the one or more markers; wherein each of the one or more tissue tags is in magnetic communication with the one or more device tags so that: (i) the one or more tissue tags and the one or more device tags repulse each other when the one or more tissue tags and the one or more device tags are moved within a predetermined distance apart; (ii) a display on a display system is created that indicated a proximity of the one or more device tags to the one or more tissue tags; (iii) a signal when the one or more device tags and the one or more tissue tags are located within a predetermined distance of each other is created; (iv) power supped to the one or more device tags when the one or more device tags and the one or more tissue tags are within a predetermined distance of each other is removed; (v) or a combination thereof.

The present teachings provide a surgical device including one or more markers that are expandable to be located at a location of interest and preferably located within a lumen of an organ. The present teachings provide one or more markers that are made of a magnetized material or in include a magnetic so that the one or more markers mark a feature of interest or provide a target within a feature of interest and/or to protect the feature of interest. The present teachings provide a surgical system that includes one or more markers and one or more insertion mechanisms that deploy the locators into a predetermined location. The present teachings provide a method of marking one or more features of interest or protecting a location proximate to a feature of interest.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a surgical system. The surgical system functions to perform a procedure on or to a target (e.g., tissue, area, region, anatomical feature). The surgical system may act upon the target so that all or a portion of a target is resected, coagulated, removed, or a combination thereof. The surgical system may include one or more surgical devices to perform a surgical procedure. The surgical system may include one or more surgical protection systems to assist in performing a procedure. The surgical system may include one or more surgical devices, one or more indicators, one or more computers, one or more surgical protection systems, one or more markers, one or more tissue effecting elements, or a combination thereof. Preferably, the surgical system includes a surgical device and a surgical protection system.

The present teachings relate to a surgical device. The surgical device may be a non-electrical device (i.e., may only provide mechanical functions such as mechanical cutting or gripping). The surgical device may be a cryogenic device. The surgical device may be a laser device. The surgical device may be a microwave device. Preferably, the surgical device is an electrosurgical device. The electrosurgical device may provide one or more therapy currents. The surgical device may include one or more needles, one or more jaws, one or more blades, one or more probes, an endoscope, bronchoscope, catheter, or a combination thereof. A therapy current may pass between the jaws (e.g., bipolar power). A therapy current may pass from a jaw to a blade or vice versa. A therapy current (e.g., monopolar power) may pass from a blade to a remote electrode (e.g., ground pad). A therapy current (e.g., bipolar power) may pass from two electrodes on the same jaw or blade. The electrosurgical device may provide microwave, cryogenics, laser, bipolar power, monopolar power, or a combination thereof to a feature of interest. The electrosurgical device may apply power before, after, or simultaneously with a mechanical technique (e.g., gripping or cutting). When power is applied an anatomical feature may be cut, cauterized, sealed, coagulated, or a combination thereof. The power supplied may cut tissue, cauterize tissue, coagulate tissue, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user. The surgical device may be or include one or more tissue effecting elements.

The one or more tissue effecting elements may function to test, remove, coagulate, stimulate, treat, a target and preferably a target tissue. The one or more tissue effecting elements may be a surgical device that extends out of a delivery device (e.g., endoscope, bronchoscope, catheter, or a combination thereof). The one or more tissue effecting elements may mechanically treat. The one or more tissue effecting elements may electrically treat. The one or more tissue effecting elements may be a blade, jaws, probe, needle, debrider, scalpel, vacuum, fluid source, or a combination thereof. The one or more tissue effecting elements may both mechanically and electrically treat a target. The one or more tissue effecting elements may include a portion of the surgical protection system. The one or more tissue effecting elements may include a portion that extends into a lumen. All of the tissue effecting elements may extend into a lumen. The tissue effecting elements may extend out of a sheath, a bronchoscope, endoscope, catheter, or a combination thereof into a lumen to act upon a target. The one or more tissue effecting elements may be in communication with an indicator or computer.

The indicator or computer may function to control the one or more tissue effecting elements, provide feedback to a user, control a portion of a surgical protection system, or a combination thereof. The indicator or computer may be in communication with the surgical device, surgical protection system, or both and may provide the user with some feedback. The indicator may include a computer or be connected to a computer. The indicator may provide a signal (e.g., haptic signal, an audio signal, visual signal, or a combination thereof). The indicator may be connected to a computer screen that may show a user where a tip of the tissue effecting element is relative to the markers, the target, or both so that a user can understand when the tip is approaching a protected area or tissue. The computer may not include an indicator or provide any indication. The computer may turn off the surgical device if the surgical device approaches the markers, the protected area or tissue, or both. For example, if the surgical device is an electrical device the electricity may be turned off if the surgical device is moved out of a region proximate to the target. The computer may be connected to an indicator that is located within the computer, within the surgical device, or both. The indicator may provide an indication to the user from the surgical device. The indicator may provide an indication from the computer. The indictor may vibrate the surgical device. The indicator may beep. The indicator may flash a light. The indicator may be separate from and connectable to the surgical device. The indicator may be reusable. The indicator may be located entirely outside of a lumen, outside of the surgical device, outside of a delivery device, or a combination thereof. The indicator may be part of the surgical protection system.

The surgical protection system may function to protect tissue, a region, an area, or a combination thereof (e.g., protected tissue) outside of a target or a target area or region. The surgical protection system may provide resistance to a surgical device if the user attempts to move the surgical device into a protected area or region. The resistance may be a physical resistance or mechanical force that resists movement of a surgical device in a direction towards protected tissue. The surgical protection system may include one or more magnets, magnetized material, magnetic field sensors, locators, insertion mechanisms, markers, tissue tags, device tags, or a combination thereof. The surgical protection system may extend within a lumen. Preferably, the surgical protection system protects a same lumen as the surgical device, the tissue effecting element, or both are located within or performing a procedure on. The surgical protection system may have a portion that is inserted into a lumen and the portion is retained within the lumen for a time while a surgery is performed. The surgical protection system may have a portion that is removable from the lumen. All or a portion of the surgical protection system may be located within, extend from, be connected to, or a combination thereof a delivery device. The surgical protection system may have a portion that is placed into a lumen by one or more locators.

The one or more locators function to deploy one or more markers to one or more locations of interest. The one or more locators may function to extend from one or more delivery devices. The one or more locators may insert a portion of a surgical protection system into a lumen. The one or more locators may locate a portion of the surgical protection system into a lumen (e.g., a marker). The one or more markers may grip tissue. The one or more markers may create a radial outward force to hold the marker in place. The one or more locators may deploy one or more markers into a lumen at one or more predetermined locations. The one or more locators may locate the markers along the lumen. The one or more locators may compress a marker, expand a lumen, or both. The one or more locators may be a portion of a delivery device (e.g., an endoscope, bronchoscope, catheter, one port of an endoscope, or a combination thereof). The one or more locators may precisely deploy a marker in a lumen. The one or more locators may include a compressed marker. The one or more locators may include a solid marker. The one or more locators may be monitored by ultrasound, x-ray, MRI, contrast medial fluoroscopy, a camera, or a combination thereof. The one or more locators may house one or more markers and the one or more markers may be located entirely within the locator. The one or more locators may be deployed by an insertion mechanism moving the one or more markers out of the locator.

The one or more insertion mechanism may function to move one or more devices (e.g., markers, tissue tags) from a locator to a location of interest or a predetermined location. The one or more insertion mechanism may be a push rod. The one or more insertion mechanisms may be a driver. The one or more insertion mechanisms may hold a device is place while the locator is retracted. The one or more insertion mechanism may insert one or more markers, or a plurality of markers within a lumen. The insertion mechanisms may move one or more markers, one or more expandable rounded members, or both into a lumen. The insertion mechanisms may move a marker in a stored state, an expanded state, or both to a predetermined location.

The one or more markers may function to mark one or more locations of interest in a lumen. Preferably, one or more markers are located within a single lumen. More preferably, two or more markers are located within a single lumen. When two or more markers are present the markers may bracket a protected region, protected tissue, a location of interest, of a combination thereof. The one or more markers may be solid (e.g., may have a predetermined size that does not change when the marker is outside of a locator). The one or more markers may be solid and not change shape, not expand, not contract, or a combination thereof. The one or more markers may be solid to completely block a lumen. The marker may stay the same size during deployment, use, removal, or a combination thereof. The marker may prevent movement through the lumen without moving the marker. Preferably, at least one of the one or more markers includes a hollow center or a hollow portion so that an effecting element can extend past the marker. The hollow center may be an opening where a device tag, surgical device, tissue effecting element, or a combination thereof may extend through the marker, tissue tag, or both. The hollow center may be shaped so that the marker is donut shaped, a torus, annular, or a combination thereof. The one or more markers may have a center that allows an effecting element to pass there through. For example, a center region of the marker may be free of material. The one or more markers preferably may be an expandable rounded member. The expandable rounded member may have a shape that is complementary to a shape of a lumen. The expandable rounded member may conform to a shape of the lumen or approximate a shape of the lumen. The lumen may have a cross-sectional shape that is round, oval, an ovoid, or a combination thereof and the expandable rounded member may conform to the shape of the lumen. The expandable rounded member may have a continuous outer section (e.g., an outer section with no begging and no end). The expandable rounded member may have an outer section that has ends which are not connected (e.g., a beginning end and an ending end that are not connected. The expandable rounded member may have a section that overlaps (e.g., one end may extend over another end). The expandable rounded member may be expandable to adjust to lumen of different sizes (e.g., a lumen that is 1 mm or more and a lumen that is 5 mm or more). The expandable rounded members may fill (e.g., match a circumference) that is about 1 mm or more, about 3 mm or more, about 5 mm or more, about 10 mm or more, about 2 cm or more, about 5 cm or more. The expandable rounded members may fill a lumen that is about 20 cm or less, about 15 cm or less, or about 10 cm or less. The expandable rounded member may extend in one direction (e.g., a primary cross-sectional direction) more than a second direction (e.g., a secondary cross-sectional direction). The expandable rounded member may be movable between a stored state and an expanded state.

The marker may have a stored state where the marker function to fit within a locator (e.g. a passage of a locator). The stored state may be where the marker is collapsed. The stored state may be where a portion of the marker is wrapped around itself one or more time. The stored state may be where the marker is elastically deformed. The stored state may be where the marker is collapsed and fitted within the locator and the locator restricts a size of the marker. The stored state may be a state of pre-deployment, post-deployment, or both. For example, the marker may be made of nitinol and may be stored in a first shape or state and then upon a condition acting upon the marker the marker may change shape to a second shape or state (e.g., expanded state). In the stored state the marker may be maintained in tension or under compression and once moved out of the locator the marker may expand into an expanded state. The marker may be subjected to a condition (e.g., heat, electricity) to change the marker from an expanded state back to a stored state or vice versa. The stored state may be a compressed expanded state. The expanded state may be a state where the marker functions to contact all or a portion of a cross-section of a lumen so that the marker is retained at a predetermined location of the lumen. In the expanded state, the marker may expand the lumen. In the expanded state, the marker may expand until a lumen prevents further expansion of the marker and the marker creates a force upon the lumen that substantially maintains the position of the marker within the lumen. The marker in the expanded state may have a cross-sectional length that is less than a maximum cross-sectional length. The cross-sectional length of the marker may vary depending upon a cross-sectional length of a lumen so that one marker may fit within an anatomical lumen of a range of size. The lumen may be a capillary, a vein, artery, trachea, mouth, nasal passage, bronchia, esophagus, stomach, colon, rectum vagina, cervix, uterus, urethra, ureter, and bladder. The marker when in the expanded state may expose one or more magnets, one or more tissue tags, or both.

The one or more tissue tags may function to connect to a marker. The one or more tissue tags may add a magnetized material, magnet, magnetic sensor, or a combination thereof to a marker. The one or more tissue tags may be a magnetic portion of the marker. The one or more tissue tags and the marker may be one monolithic structure. For example, the marker may be made of a magnetic material that is magnetized so that the marker acts as a tissue tag. The one or more tissue tags may be connected to the marker. The one or more tissue tags may be inserted into the marker. The one or more tissue tags may be connected on an outside of the marker. The one or more tissue tags may include one or more magnets. The one or more tissue tags may each have a predetermined magnetic orientation so that when installed a first polarity (e.g., South) faces one direction and a second polarity (e.g., North) faces in an opposing direction. The magnetic orientation may be aligned with the axis of the lumen. For example, north may face distally and south may face proximally or vice versa. The magnetic orientation may be changed once installed so that a desired magnetic orientation may be selected. The magnetic orientation may be switched by physically repositioning the tissue tags (e.g., magnet); remagnetizing the magnets, reversing a current direction, or a combination thereof. The tissue tags may have a magnetic orientation that is the same as the magnetic orientation of a device tag (e.g., so that they are attracted together). For example, magnets of the tissue tags and the magnets of the device tags may have their polarity face in the same direction. Preferably, the tissue tags have a magnetic orientation that is opposite to the magnetic orientation of the device tag (e.g., so that the two repel each other). For example, the north polarity of the tissue tags may face distally and the north polarity of the device tag may face proximally so that the south polarities face each other to create a repelling force axially along the lumen. The polarities of the tissue tags, device tags, or both may be separated along the axis of the lumen. The tissue tags may repel a device tag in a direction that is axially along a lumen. The repulsion forces may move or repel the device tag away from tissue tags in an axial direction of the lumen. The device tag and the tissue tag may be deployed within a same lumen at a same time. The tissue tags may be at least partially embedded into the marker so that the tissue tags are supported by the marker and retained in place within a lumen. The tissue tags may be located on an inside of a marker (e.g., inner circumference). The tissue tags may be located substantially collinear with a location of a device tag. For example, the tissue tags may be annular in shape and may be an annular ring that forms the hollow center of the marker and the device tag may be located in a same plane or line with the tissue tags. A portion of a device may extend through the tissue tags. The tissue tags may be rectangular, square, oval, circular, or a combination thereof. Each marker may include one tissue tag. Each marker may include a plurality of tissue tags. The one or more tissue tags may be centrally located on the marker. The one or more tissue tags may be located evenly spaced apart along a circumference of the marker. The one or more tissue tags may extend from a first end region to a second end region along an axis of the lumen so that the first end region has a portion of the marker with a first polarity and a second end region has a portion of the marker with a second polarity. The one or more tissue tags may be entirely made of a magnetized material. The one or more tissue tags may have a magnetized portion. The one or more tissue tags may be a sensor that senses a magnetic orientation, magnetic field strength, or both from a device tag (e.g., determines which direction the polarity is facing (e.g., distally or proximally)). The tissue tags may have magnets that are made of or include: iron, nickel, cobalt, rare earth metals, samarium cobalt, neodymium iron boron, lanthanide, or a combination thereof. The tissue tags may create a magnetic orientation (e.g., a direction the poles face) that is detectable by the device tag, repels a device tag, attracts a device tag, or a combination thereof.

The magnetic field may function to create one or more zones, separate portions of a lumen, alert a user as to movement of a device tag or tissue effecting element approaching a protected area or protected tissue. For example, the separate portions may be along a longitudinal axis of a lumen. The magnetic field may be separated along an axis of a lumen. For example, one side of a marker (e.g., distal side) may have a first magnetic field (e.g., a north or south polarity) and a second side of a marker (e.g., proximal side) may have a second magnetic field (e.g., a polarity that is opposite the first side, thus, if the first side is north then the second side is south). The magnetic field may extend a pre-determined distance from the marker. The magnetic field of one tag (e.g., device tag) may repel or be repelled by a magnetic field of another tag (e.g., tissue tag) by a predetermined amount of force or strength. The strength of the magnetic field may be varied depending on the type of procedure, the location of a procedure, the user desires, or a combination thereof. The magnetic field strength (e.g., repelling force) may provide a resistance or movement force of about 0.5 N or more, about 1 N or more, about 1.5 N or more, or about 2 N or more. The magnetic field strength may have a resistance or movement force of about 25 N or less, about 20 N or less, about 15 N or less, or about 10 N or less. The magnetic field may extend sufficiently far from the marker, the tissue tag, or both so that the magnetic field of the tissue tag is realized before a device tag contacts the marker. The magnetic field may be sufficiently strong to move tissue or a protected issue. The magnetic field may be detectable a distance of about 1 mm or more, about 3 mm or more, about 5 mm or more, about 7 mm or more, or about 1 cm or more. The magnetic field may be detectable a distance of about 10 cm or less, about 7 cm or less, about 5 cm or less, or about 3 cm or less. A tissue tag magnetic field sensor may be used in place of magnet on the tissue tag.

One or more tissue tag magnetic field sensors may be connected to one or more tissue tags. The tissue tag may be a tissue tag magnetic field sensor. The one or more tissue tag magnetic field sensors may be used instead of a magnet. The one or more tissue tag magnetic field sensors may provide feedback to a user so that the user is warned if a surgical device, or effecting element extends outside of a target region or zone into a protected region or zone. The one or more tissue tag magnetic field sensors may be connected to or in communication with an indicator, a computer, or both. The one or more tissue tag magnetic field sensors may be wirelessly connected to an indicator, a computer, or both. The one or more tissue tag magnetic field sensors may be connected to an indicator, a computer, or both by a wire. The tissue tag magnetic field sensor may be an electronic magnetometer, a microchip, a hall effect sensor, magneto-diode, magneto-transistor, AMR magnetometer, GMR magnetometer, magnetic tunnel junction magnetometer, magneto-optical sensor, MEMS compass, fluxgate magnetometer, or a combination thereof. The tissue tag magnetic field sensor may sense a distance between the tissue tags and the device tags and upon the distance dropping below a predetermined distance a signal or warning may be provided to a user. For example, if the tissue tag and device tag are within 5 cm or each other than an auditory signal, haptic signal, visual indication, or combination thereof may occur. The tissue tag magnetic field sensor may provide feedback when a distance between the tissue tag and device tag is about 50 cm or less, about 40 cm or less, 30 cm or less, about 20 cm or less, or about 10 cm or less. The tissue tag magnetic field sensor may provide feedback when a distance is about 5 mm or more, about 1 cm or more, or about 5 cm or more. The tissue tag magnetic field sensors may provide a feedback to a monitor so that the monitor may display a distance between a device tag and a tissue tag. For example, the monitor may display a distance between two markers and may show the tissue tag as the device tags approach the tissue tags so that the user is visually aware of the proximity of the tissue tag and device tag relative to each other.

The one or more device tags may function to connect to a surgical device. Preferably, the device tags indicate a distal most position, a position of an operational portion of a medical device, or a combination thereof. The one or more device tags may be located at or on one or more positions of a tissue effecting element. The one or more device tags may be located within a tip of the one or more tissue effecting elements. The one or more device tags may be located proximate from a tip of a tissue effecting element. The tissue effecting element may include two or more device tags. For example, one device tag may be in a distal end of the tissue effecting element and may be in communication with a first tissue tag and a second device tag may be proximal to the distal end and may be in communication with a second tissue tag so that the user is guided to the target region between the two tissue tags. The one or more device tags may be substantially identical to the tissue tags except that the device tags may be incorporated into a surgical device or a tissue effecting element. The one or more device tags may include a magnetized material, magnet, magnetic sensor, or a combination thereof to a surgical device or tissue effecting element that may be added to a surgical device. The one or more device tags may be a magnetic portion of the surgical device or tissue effecting element. A magnetic orientation of the one or more device tags may be aligned along an axis or longitudinal direction of a lumen. The one or more device tags and the surgical device or tissue effecting element may be one monolithic structure. For example, a portion of the surgical device or tissue effecting element (e.g., tip) may be made of a magnetic material that is magnetized so that the device acts as a device tag. The one or more device tags may be connected to the surgical device or tissue effecting element. The one or more device tags may be inserted into the surgical device or tissue effecting element. The one or more device tags may be connected on an outside of the surgical device or tissue effecting element. The one or more device tags may include one or more magnets. The one or more device tags may have predetermined polarity directions so that when installed or inserting into a lumen a first polarity (e.g., South) faces one direction and a second polarity (e.g., North) faces in an opposing direction. The device tags and tissue tags may have common polarities (i.e., both are north or both are south). When the device tags and the tissue tags have common polarities the device tags and the tissue tags may have an increase in resistance as a user attempts to move the device tag towards a tissue tag. The common polarities may create a repelling force. The repelling force may create an increased tactile resistance as a distance of a device tag and a tissue tag becomes smaller. The repelling force may create a force that is an increased imparting force upon the device tag to restrict a device from contacting protected tissue, a protected area, a protected region, or a combination thereof. The repelling force may create a force that is an increased imparting force upon the tissue marker and displaces the tissue marker and the associated protected tissue away from the device tip. The repelling force may be sufficiently strong that the marker, the tissue tag, the feature of interest, the protected tissue, or a combination thereof are moved as the device tag approaches the marker so that the tip of the surgical device is prevented from contacting the protected issue. For example, if the lumen is a colon and device tag approaches the tissue tag the colon may move so that the surgical device is prevented from contacting the protected tissue. The magnetic orientation may be changed once installed so that a desired magnetic orientation may be selected (e.g., north may be switched from distal to proximal or vice versa). The magnetic orientation may be switched by physically repositioning the device tags (e.g., magnet); remagnetizing the magnets, reversing a current direction, or a combination thereof. The tissue tags may have a magnetic orientation that is the same as the magnetic orientation of a device tag (e.g., so that they are attracted together). Preferably, the tissue tags have a magnetic orientation that is opposite as the magnetic orientation of the device tag (e.g., so that the two repel each other). The device tags may be at least partially embedded into the surgical device or tissue effecting element so that the tissue tags are supported by the surgical device or tissue effecting element and move within a lumen. The device tags may be located on an inside of a surgical device or tissue effecting element (e.g., inside of a tip or stylet). The tissue tags may be located substantially collinear with a location of a device tag. A device tag may be located on each side of a tissue tag. The device tags may be rectangular, square, oval, circular, or a combination thereof. Each surgical device or tissue effecting element may include one device tag. Each surgical device or tissue effecting element may include a plurality of device tags. The one or more device tags may be centrally located on the surgical device or tissue effecting element. Preferably, the device tags are located in a tip of surgical device or tissue effecting element. The one or more device tags may be located evenly spaced apart along a surgical device or tissue effecting element (e.g., a stylet). The one or more device tags may be entirely made of a magnetized material. The one or more device tags may have a magnetized portion. The one or more device tags may be a sensor that senses a magnetic orientation from a tissue tag. The device tags may have magnets that are made of or include: iron, nickel, cobalt, rare earth metals, samarium cobalt, neodymium iron boron, lanthanide, or a combination thereof. The device tags may create a magnetic orientation that is detectable by the tissue tag, causes a repelling force between a device tag and a tissue tag, creates an attracting force between a device tag and a tissue tag, or a combination thereof. The one or more device tags may be partially or entirely located within surgical device or tissue effecting element. The one or more device tags may be partially or entirely located external of a surgical device or tissue effecting element. Preferably, the device tag is located within or on a tip or tip region of a surgical device or tissue effecting element. The tip of the device may be a distal most end of the surgical device or tissue effecting element. The device tag may be located proximate to, above, before, after, over, or a combination thereof an active portion of a surgical device. For example, if the surgical device is a debrider then the active portion is the blades of the debrider. If the surgical device is a scalpel then the active portion is the blade. If the surgical device is a needle then the active portion is a tip of the needle. If the surgical device is an electric device (e.g., bipolar or monopolar) then the active portion is any portion of the device that provides a therapy current to the target. The device tag may protect the target by providing the user an indication when the active portion is located near, proximate to, moving toward, or a combination thereof the protected are around the target. The active portion may be located proximal of a distal end of the surgical device or tissue effecting element. The device tag may have a device tag magnetic orientation that extends distal of the tip, the active portion, or both so that an indication or signal (e.g., resistance of an opposing magnet, a visual signal, an audible signal, a haptic signal, pulling of an opposing magnet) may be provided before the effecting element contacts the marker or extends over a protected area or protected tissue.

The device tag magnetic orientation functions to repel the device tag or attract the device tag to the tissue tag. Preferably, the device tag has an orientation so that the device tag and the tissue tag repel each other. The device tag magnetic orientation may be opposite the magnetic orientation of the tissue tag (e.g., north sides and south sides may be located apart from each other (e.g., north of the device tag may face proximally and north of the tissue tag may face distally so that the south poles align and device tag and the tissue tag repel each other)). The device tag magnetic orientation may be the same as the magnetic orientation of the tissue tag (e.g., north and north will both face distally or proximally). The teachings herein for the magnetic orientation of the tissue tag are expressly incorporated by reference herein for the device tag orientation and vice versa. The device tag magnetic orientation may function to create one or more zones, separate portions of a lumen, alert a user as to movement of a device tag or tissue effecting element approaches a protected area or protected tissue. For example, the separate portions may be along a longitudinal axis of a lumen. The magnetic orientation may be separated along an axis of a lumen. For example, one side of a surgical device or tissue effecting element may have a first magnetic orientation (or polarity) and a second side of a surgical device or tissue effecting element may have a second magnetic orientation (or polarity). The magnetic orientation may extend a pre-determined distance from the marker. The device tag magnetic orientation may extend sufficiently far from a surgical device or tissue effecting element so that the magnetic field of the tissue tag is realized before a device tag contacts the marker. A device tag magnetic field sensor may be used in place of magnet on the device tag.

The device tag magnetic field sensor may function to sense a tissue tag, a location relative to a tissue tag, a target, a field of a tissue tag, or a combination thereof and provide an indication when located within a predetermined distance of the tissue tags. One or more device tag magnetic field sensors may be connected to or located within one or more device tags. The device tag may be a device tag magnetic field sensor. The one or more device tag magnetic field sensors may be used instead of a magnet. The one or more device tag magnetic field sensors may provide feedback to a user so that the user is warned if a surgical device or effecting element extends outside of a target region or zone into a protected region or zone; if the device tag moves too close to a target tag; or both. The one or more device tag magnetic field sensors may be connected to or in communication with an indicator, a computer, or both. The one or more device tag magnetic field sensors may be wirelessly connected to an indicator, a computer, or both. The one or more device tag magnetic field sensors may be connected to an indicator, a computer, or both by a wire. The device tag magnetic field sensor may be an electronic magnetometer, a microchip, a hall effect sensor, magneto-diode, magneto-transistor, AMR magnetometer, GMR magnetometer, magnetic tunnel junction magnetometer, magneto-optical sensor, MEMS compass, fluxgate magnetometer, or a combination thereof. The device tag magnetic field sensor may sense a distance between the tissue tags and the device tags and upon the distance dropping below a predetermined distance a signal or warning may be provided to a user. For example, if the tissue tag and device tag are within 5 cm or each other than an auditory signal, haptic signal, visual indication, or combination thereof may occur. The device tag magnetic field sensor may provide feedback when a distance between the tissue tag and device tag is about 50 cm or less, about 40 cm or less, 30 cm or less, about 20 cm or less, or about 10 cm or less. The device tag magnetic field sensor may provide feedback when a distance is about 5 mm or more, about 1 cm or more, or about 5 cm or more. The device tag magnetic field sensors may provide a feedback to a monitor so that the monitor may display a distance between a device tag and a tissue tag. For example, the monitor may display a distance between two markers and may show the tissue tag as the device tags approach the tissue tags so that the user is visually aware of the proximity of the tissue tag and device tag relative to each other. The tissue tag magnetic field sensor, the device tag magnetic field sensor, or both may provide an indication or signal when the surgical device, a tip, a tissue effecting element, or a combination thereof move within a restricted region.

The restricted area may function to be a region proximate to a protected area or region where a signal is created, an indication is created, two magnetic fields overlap, or a combination thereof. The restricted area may be a region where a target area and a protected area overlap or intersect. The restricted area may be an area where power is cut off from an electrosurgical device, power is disconnected from the surgical device, poles of the tissue tag and poles of the device tag repel each other, or a combination thereof. The restricted area may be an area within about 10 cm or less of a tissue tag, about 7 cm or less of a tissue tag, or about 5 cm or less of a tissue tag (e.g., within about ±5 mm). The restricted area may be an area within about 1 mm or more, about 3 mm or more, about 5 mm or more, about 7 mm or more, or about 1 cm or more. The surgical protection system may include one or more restricted areas. The surgical protection system may include restricted areas that book end a device tag so that the device tag may operate within a region created by the tissue tags, the device tag may only allow the surgical device to work between restricted regions, the device tag may be repelled towards a target, or a combination thereof. The restricted areas may be located on one or both sides of a tissue tag. The restricted area may protect an organ, a protected region or an organ, a protected area of a lumen, or a combination thereof.

The organ may be any organ that includes a lumen, forms a lumen, includes tissue that requires protecting, is located proximate to sensitive tissue, or a combination thereof. The organ may be one or more of a rectum, ear canal, throat, nasal passage, urethra, vaginal canal, an artery, a vein, small intestine, large intestine gastrointestinal tract; respiratory system; or a urological system. Preferably, the organ is a colon and the colon is a lumen. The lumen may be any generally tubular anatomical feature that is part of an organ. The lumen may have a generally circular cross-sectional shape. The lumen may include one or more natural openings. For example, the lumen may be accessed without cutting any tissue. The lumen may include one or more targets. The targets may be an area of interest. The targets may be an area that is a subject of a surgery. The targets may be an area, a region, or both of a lumen. The target may be partially removed or fully removed. The target may be located near or around one or more protected areas, protected regions, or a combination thereof. The protected area or region may be part of a lumen or surrounding structure that is healthy, may contaminate a surgical site, may be sensitive to the procedure being performed, or a combination thereof. The protected area may be located on one or both sides of the target. The protected areas or region may be separated by one or more targets.

The surgical protection system may be deployed using a method. The method may be performed using one or more of the steps taught herein that may be performed in any order unless specifically specified. One or more locators may be inserted into a lumen. One or more markers may be deployed from the locator by depressing one or more insertion mechanism. The locator may be removed. The same or a new locator may be inserted into the lumen. Additional markers may be inserted into the lumen. The locators may be moved axially along the lumen to deploy the markers at one or more axial locations along the lumen. When two or more markers are deployed the markers are axially separated with a target located therebetween. The additional markers may be inserted into the locator while the locator is within the lumen. The additional markers (e.g., one or more, two or more) may be deployed while the locator is located within the lumen. The markers may automatically expand. A stimuli may be applied to the markers to expand the markers. One or more surgical devices may be inserted into the same lumen as the markers. The surgical device may extend through one or more markers. A tissue effecting element may extend through the one or more markers. The tissue effecting element may be located proximate to a target. The tissue effecting element may include one or more device tags. The device tags when moved proximate to the tissue tags may create a resistive force, an indication, a signal, or a combination thereof that assists in protecting a protected area, protected region, protected tissue, or a combination thereof. The tissue effecting element may be moved back into a surgical device, endoscope, bronchoscope, catheter, or a combination thereof. The surgical device may be removed from the lumen. The delivery device may be removed from a lumen. The markers may be removed from a lumen. A stimuli may be applied to the markers to contract the markers. Only one marker may be deployed. The device tag may be repulsed from the tissue tag. The tissue effecting element with a device tag may be inserted into a same lumen as the one or more tissue tags. A display device or display system may display the current position of the one or more tissue tags relative to the one or more device tags. A signal may be created when the device tags and the tissue tags are within a distance of each other. Power may be removed when the device tags and the tissue tags are located within a predetermined distance of each other. Power may be suppled when the device tags and the tissue tags are located within or outside of a predetermined distance of each other. A second marker may be deployed within a same lumen as a first marker. A tip may be inserted through a hollow center in a marker.

Figure 1:
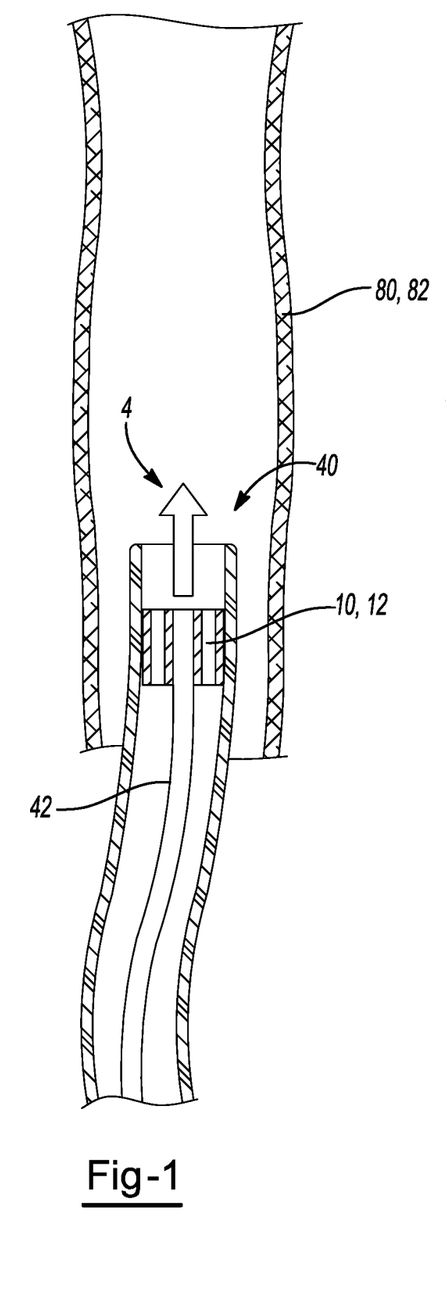
FIG. 1 is a marker in a locator in an unexpanded state.

FIG. 1 illustrates a surgical device 4 of a surgical system inserting a marker 10 that in a stored state 12 into a lumen 82 of an organ 80. The surgical device 4 is a locator 40 that locates the marker 10 at a predetermined site. The marker 10 is expelled from the locator 40 via an insertion mechanism 42 that moves the marker 10 out of the locator 40 into the lumen 82.

Figure 2:
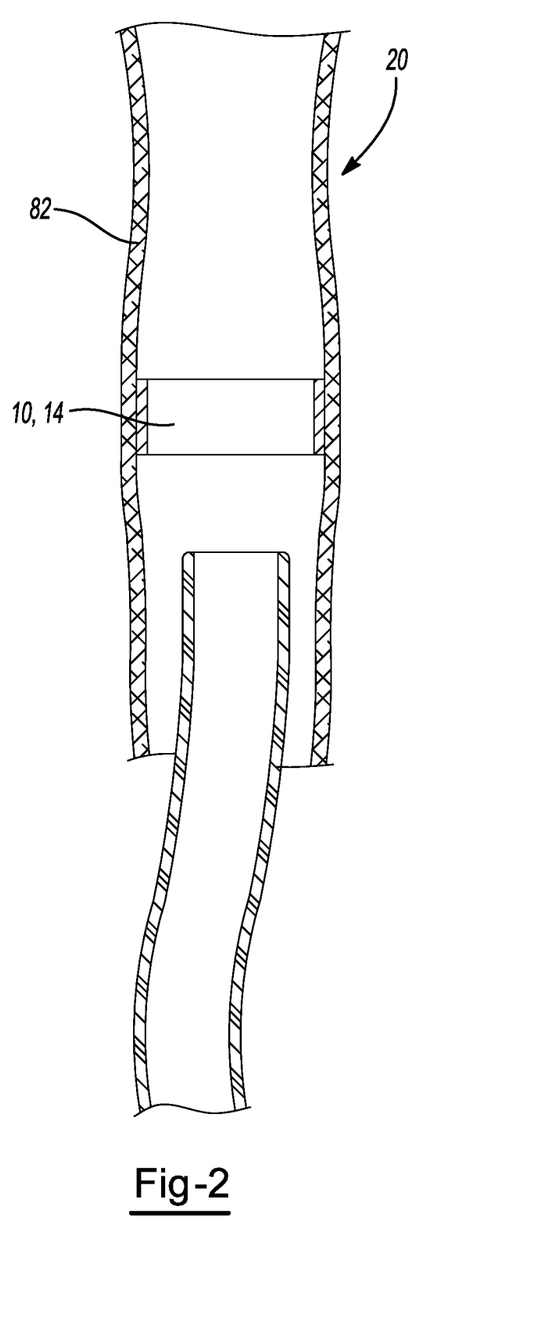
FIG. 2 is a marker outside of a locator in an expanded state.

FIG. 2 illustrates the marker 10 in an expanded state 14, where the marker 10 is an expandable rounded member 20 that expands into contact with the lumen 82.

Figure 3:
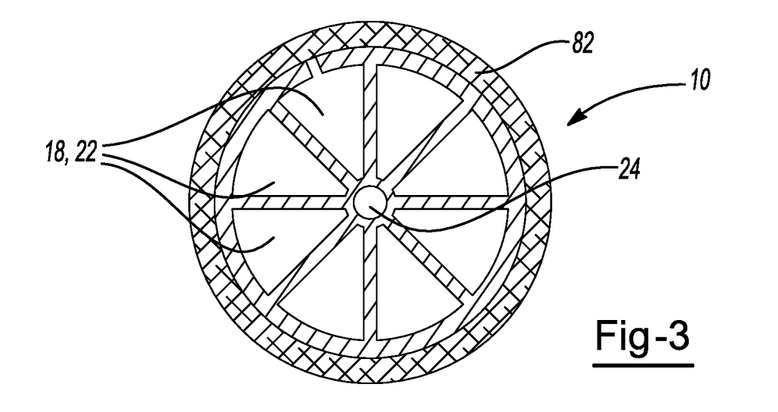
FIG. 3 is a top view of a marker located within a lumen

FIG. 3 is a top view of the marker 10 in contact with the lumen 82. The marker 10 includes tissue tags 22 that are magnets 18 or are magnetized. The marker 10 is an expandable rounded member 20 having a hollow center 24.

Figure 4A:
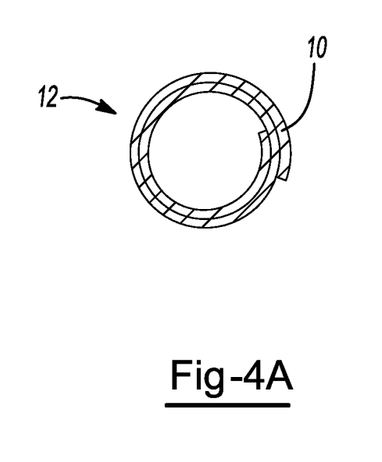
FIG. 4A is a marker in an unexpanded state

FIG. 4A illustrates a marker 10 in a stored state 12.

Figure 4B:
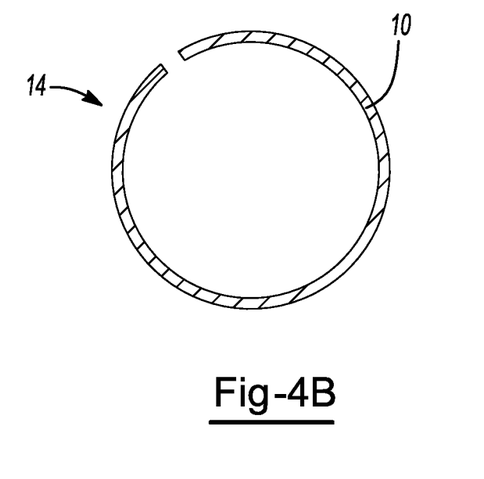
FIG. 4B is a marker in an expanded state.

FIG. 4B illustrates a marker 10 in an expanded state 14.

Figure 5A:
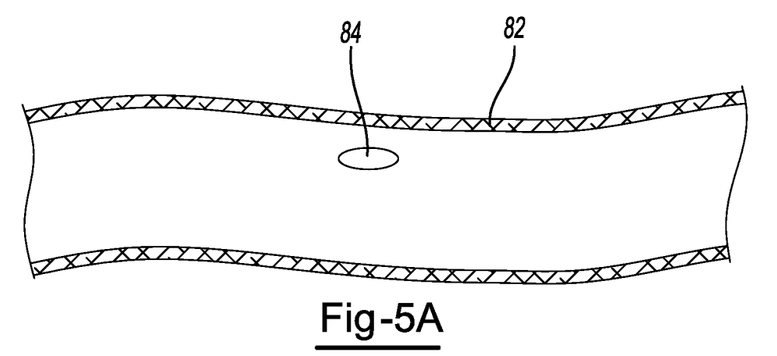
FIG. 5A is a lumen having a target of interest.

FIG. 5A illustrates a lumen 82 with a feature of interest that is the target 84 of a procedure.

Figure 5B:
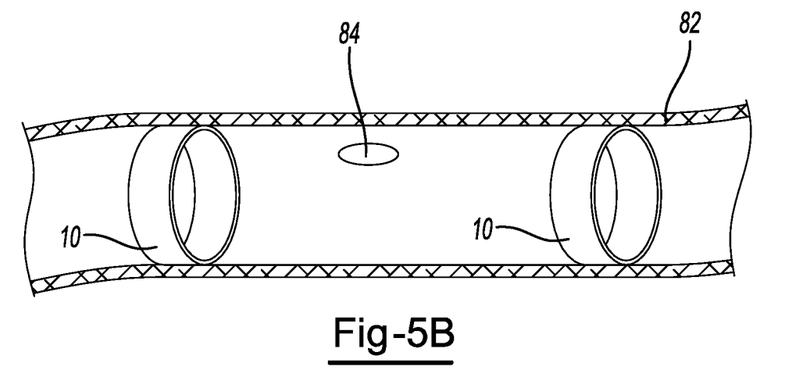
FIG. 5B is a lumen having tissue tags located before and after a target.

FIG. 5B illustrates a lumen 82 having a feature of interest that is the target 84 of a procedure. The target 84 is located between two markers 10 that are located within the lumen 82.

Figure 5C:
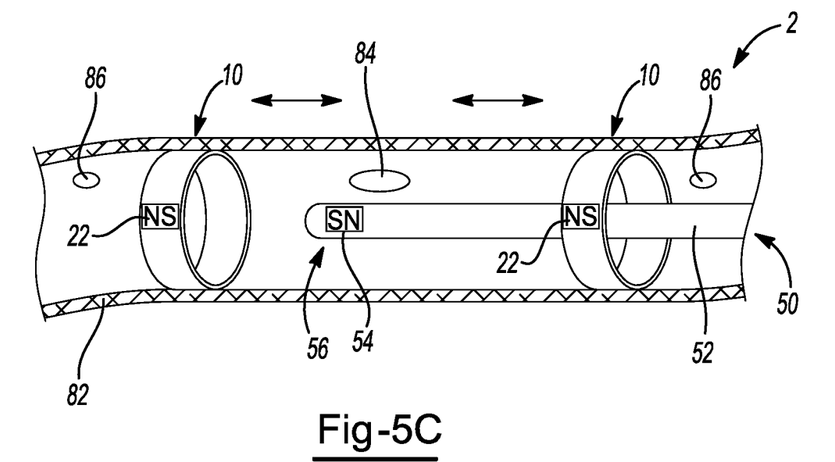
FIG. 5C is a lumen having tissue tags and a tip of a surgical device, having a device tag, extending through one of the tissue tags and being located between the two tissue tags so that the device tag provides an indication when approaching the tissue tags.

FIG. 5C illustrates a surgical system 2 with markers 10 located within a lumen 82. The lumen 82 includes a target 84 located between a pair of markers 10. Each marker 10 includes a tissue tag 22 with a magnetic orientation (e.g., the north polarity of the tissue tags 22 faces distally and the north polarity of the device tag 54 faces proximally). The markers 10 are located between the target 84 and a protected 86 area or tissue so that the markers 10 and tissue tags 22 protect the protected 86 area or tissue. A surgical protection system 50 having a tissue effecting element 52 has a tip 56 that extends between the markers 10 so that the tissue effecting element 52 can perform a procedure on the target 84 area or tissue. The tip 56 of the tissue effecting element 52 includes a device tag 54 that maintains the tip 56 between the markers so that the protected 86 area or tissue is protected from being acted upon by the tissue effecting element 52. The device tag 54 includes a magnetic orientation that as shown is the opposite of the tissue tags 22 so that the tissue effecting element 52 is repelled as the tip 56 approaches either marker 10.

Figure 5D:
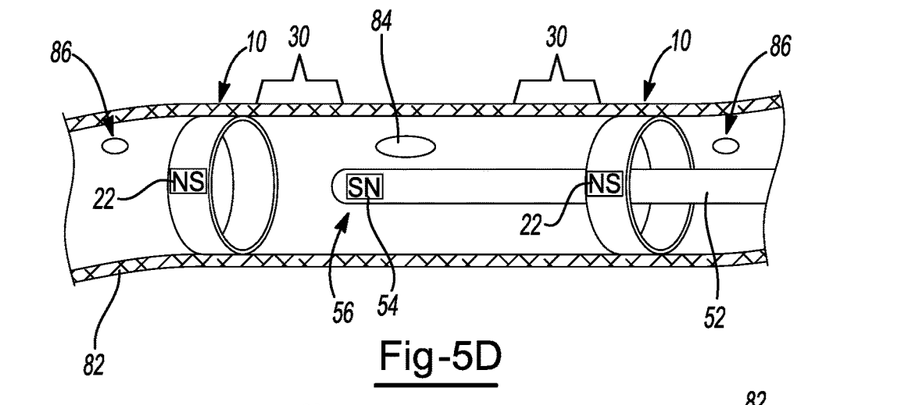
FIG. 5D is a lumen having a pair of tissue tags with a device tag extended beyond the target.

FIG. 5D illustrates a tissue effecting element 52 having a tip 56 including a device tag 54 with a magnetic orientation. There are two markers 10 located within a lumen 82. The markers 10 each include a tissue tag 22 with a magnetic orientation. The markers 10 are located between two protected 86 tissues or areas and a target 84 is located therebetween. If the device tag 54 extends in a restricted area 30 the tissue tag 22 will repel the device tag 54 so that a user will feel an increase in resistance or the protected tissue is displaced away from the tip.

Figure 6:
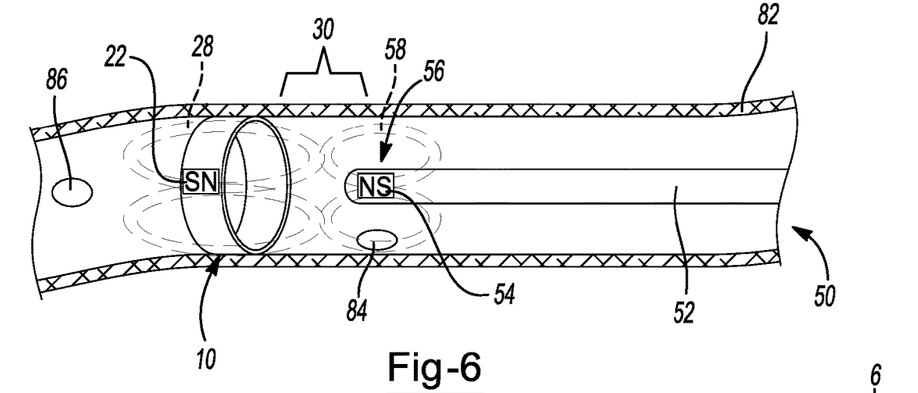
FIG. 6 illustrates a magnetic field of a tissue tag repelling a device tag.

FIG. 6 illustrates a marker 10 located within a lumen 82 between a target 84 and protected 86 area or tissue. The marker 10 includes a tissue tag 22 that is magnetized and generates a magnetic field 28. The surgical protection system 50 includes a tissue effecting element 52 including a tip 56 with a device tag 54 that is magnetized or magnetic and creates a device tag magnetic field 58. When the tip 56 comes proximate to the marker 10 the magnetic field 28 and the device tag magnetic field 58 create a restricted area 30 that restricts movement of the tip 56 towards the protected 86 tissue or area or provides some resistance of movement of the tip 56 or the protected tissue is displaced away from the tip.

Figure 7:
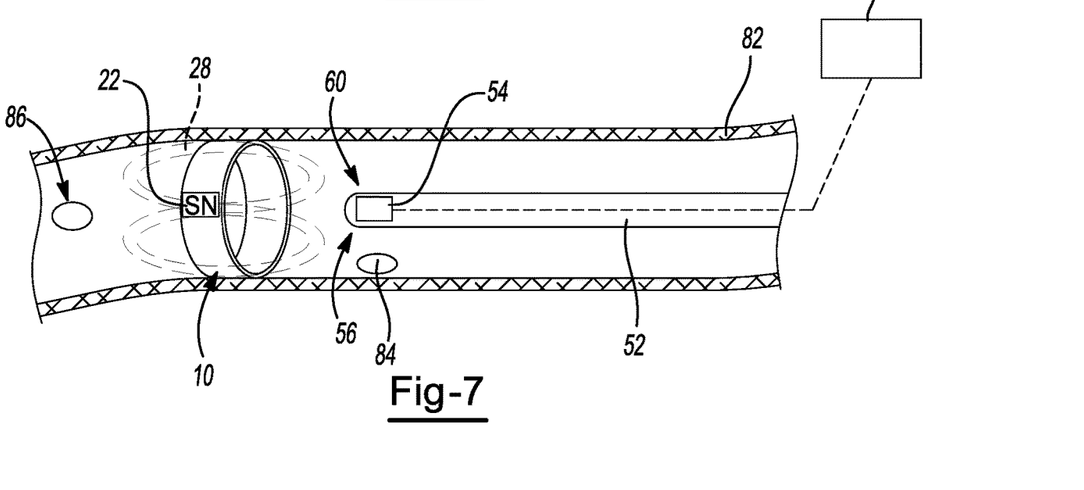
FIG. 7 illustrates a magnetic field of a tissue tag relative to a tip of a surgical device.

FIG. 7 illustrates a marker 10 located within a lumen 82 between a target 84 and protected 86 area or tissue. The marker 10 includes a tissue tag 22 that is magnetized and generates a magnetic field 28. A tissue effecting element 52 has a tip 56 including a device tag 54. The device tag 54 is a device tag magnetic field sensor 60 that is connected to a computer or indicator 6 that provides a signal to the user when the tip 56 approaches the magnetic field 28 of the tissue tag 22 so that a surgeon is warned, or the power is turned off when the tip 56 approaches the marker 10 and the protected 86 area or tissue is protected.

Figure 8:
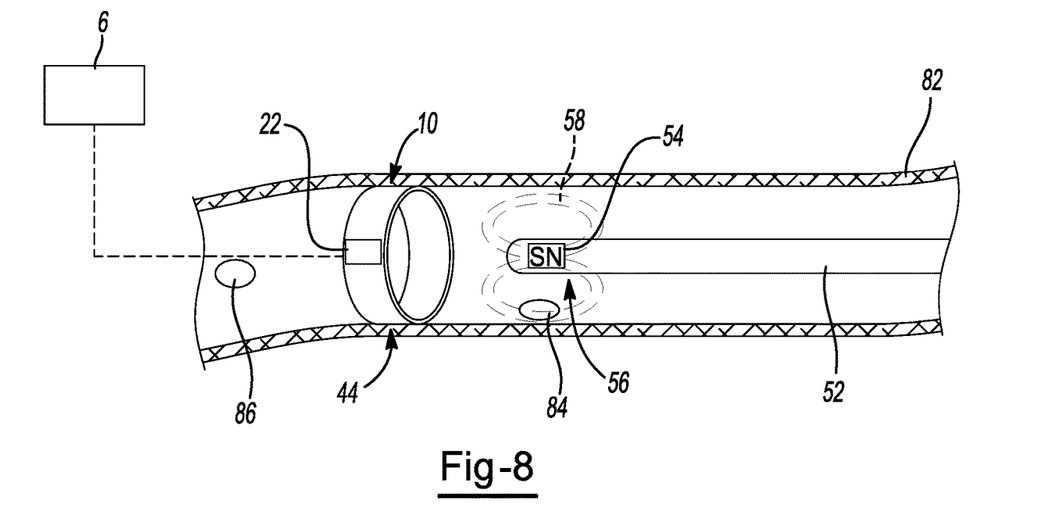
FIG. 8 illustrates a magnetic field of a device tag located proximate to a marker.

FIG. 8 illustrates a marker 10 located within a lumen 82 between a target 84 and a protected 86 area or tissue. The marker 10 includes a tissue tag 22 that is in communication with computer or indicator 6 via a tissue tag magnetic field sensor 44. The tissue effecting element 52 has a tip 56 including a device tag 54 that creates a device tag magnetic field 58. As the device tag 54 approaches the tissue tag 22 the computer or indicator 6 provides a signal to a user so that the protected 86 tissue or area is not damaged.

Figure 9:
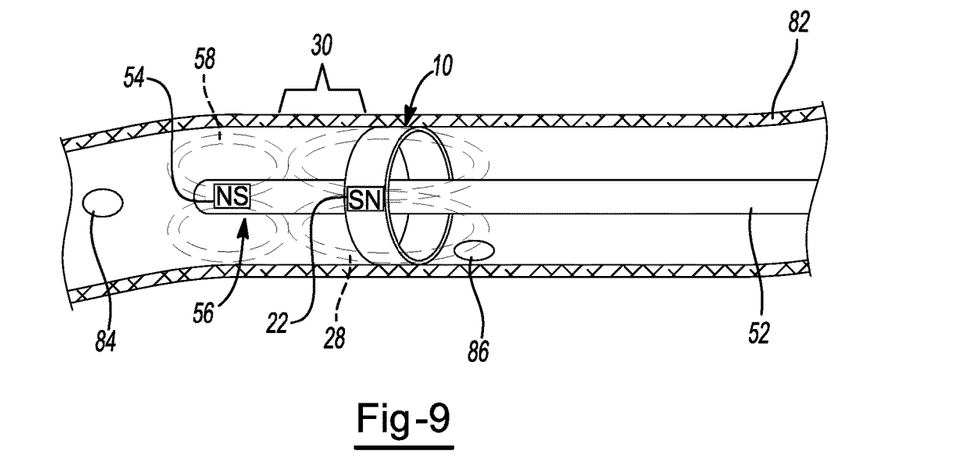
FIG. 9 illustrates a device tag within a tip of a surgical device that has extended through a marker having a tissue tag where the magnetic poles are proximate to one another.

FIG. 9 illustrates a marker 10 located between a target 84 and a protected 86 area or region. The marker 10 includes a tissue tag 22 having a magnetic field 28. A tissue effecting element 52 is extended past the marker 10 so that the tissue effecting element can act upon the target 84. The tissue effecting element 52 has a tip 56 including a device tag 54 with a device tag magnetic field 58. The device tag magnetic field 58 and the magnetic field 28 of the marker 10 when proximate to each other create a restricted area 30 where the tissue tag 22 and the device tag 54 are repelled.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. Unless otherwise stated, a teaching with the term "about" or "approximately" in combination with a numerical amount encompasses a teaching of the recited amount, as well as approximations of that recited amount. By way of example, a teaching of "about 100" encompasses a teaching of within a range of 100+/−15.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Surgical System
4 Surgical Device
6 Indicator/Computer
10 Marker
12 Stored State
14 Expanded State
18 Magnets
20 Expandable Rounded Member
22 Tissue Tags
24 Hollow Center
26 Solid Marker
28 Magnetic Field
30 Restriction Area
40 Locator
42 Insertion Mechanism
44 Tag Magnetic Field Sensor
50 Surgical Protection System
52 Tissue Effecting Element
54 Effecting Element Markers Device Tag
56 Tip
58 Device Tag Field
60 Effecting Magnetic Field Sensor
80 Organ
82 Lumen
84 Target
86 Protected

We claim:
1. A surgical system comprising:
one or more tissue effecting elements including a tip;
one or more device tags connected to the one or more tissue effecting elements, each of the one or more device tags having a spatial relationship and magnetic orientation with the tip of the one or more tissue effecting elements; and an insertion mechanism including a device comprising:
plurality of markers, two or more of which are expandable rounded members that are positionable in a same lumen in an organ, the expandable rounded members being expandable from a stored state to an expanded state and when in the expanded state each of the expandable rounded members are configured to expand to move into contact with the lumen in the organ; and
wherein each of the expandable rounded members comprise a tissue tag, each of the tissue tags being magnetized or comprising a magnet;
wherein the expandable rounded members are configured to be located within and deployed from the insertion mechanism into the lumen in the organ at a predetermined location relative to the target tissue;
wherein the one or more tissue effecting elements are longitudinally movable relative to each of the expandable rounded members; and
wherein the tissue tags are removable from the lumen by contracting the expandable rounded members and withdrawing the expandable rounded members from the lumen;
wherein the one or more device tags present a magnetic field of common polarity respectively with each of the tissue tags of the device so that the one or more device tags provide an increase in tactile resistance to the tip of the one or more tissue effecting elements moving towards the tissue tags, the target tissue and the tissue tags are displaced as the one or more device tags are configured to be moved towards the target tissue and the tissue tags.

2. The surgical system of claim 1, wherein all or a portion of the expandable rounded members of the plurality of markers are made of nitinol.

3. The surgical system of claim 1, wherein the expandable rounded members of the plurality of markers include a hollow center.

4. The surgical system of claim 1, wherein some of the markers include one or more solid markers that are configured to be deployed into the lumen, the one or more solid markers comprising at least one of a predefined size or a predefined shape.

5. The surgical system of claim 1, wherein the device has a magnetic orientation that repels the one or more device tags.

6. The surgical system of claim 1, wherein at least one of the one or more tissue effecting elements is a blade or a needle.

7. The surgical system of claim 1, further comprising at least one of:
a. a display system configured to indicate a proximity of the tip of the one or more tissue effecting elements to the plurality of markers;
b. an alarm system configured to provide a signal when the tip of the one or more tissue effecting elements is located within a predetermined distance from each of the plurality of markers; or
c. means for removing power supplied to the tip when the tip of the one or more tissue effecting elements is located within a predetermined distance from each of the plurality of markers.

8. The surgical system of claim 7, wherein the signal is an auditory, visual, haptic, or a combination thereof signal.

9. The surgical system of claim 7, wherein the power supplied to the tip cuts tissue, cauterizes tissue, coagulates tissue, or a combination thereof.

10. The surgical system of claim 7, wherein the tissue tags are configured to be inserted into the same lumen and surgery is performed on that lumen.

11. The surgical system of claim 7, wherein the plurality of markers comprise two markers that are adapted to bracket a surgical site and the one or more device tags includes a device tag located between the two markers.

12. A surgical system comprising:
one or more tissue effecting elements including a tip;
one or more device tags connected to the one or more tissue effecting elements, each of the one or more device tags having a spatial relationship and magnetic orientation with the tip of the one or more tissue effecting elements;
an insertion mechanism including a device comprising:
one or more markers, some or all of which are expandable rounded members that are expandable from a stored state to an expanded state and when in the expanded state each of the expandable rounded members are configured to expand to move into contact with a lumen in an organ, the lumen defining a longitudinal axis; and
wherein each of the expandable rounded members comprise a tissue tag, each of the tissue tags being magnetized or comprising a magnet;
wherein the expandable rounded members are configured to be located within and deployed from the insertion mechanism into the lumen in the organ at a predetermined location relative to the target tissue;
wherein the one or more tissue effecting elements are longitudinally movable relative to each of the expandable rounded members in a direction that extends along the longitudinal axis of the lumen; and
a power circuit operable to remove power supplied to the tip when the tip and the one or more markers are within a predetermined distance of each other;
wherein the one or more device tags present a magnetic field of common polarity respectively with each of the tissue tags of the device so that the one or more device tags provide an increase in tactile resistance to the tip of the one or more tissue effecting elements moving towards the tissue tags, the target tissue and the tissue tags are displaced as the one or more device tags are configured to be moved towards the target tissue and the tissue tags.

13. A surgical system comprising:
one or more tissue effecting elements including a tip;
one or more device tags connected to the one or more tissue effecting elements, each of the one or more device tags having a spatial relationship and magnetic orientation with the tip of the one or more tissue effecting elements;
an insertion mechanism including a device comprising:
plurality of markers, two or more of which are expandable rounded members that are positionable in a same lumen in an organ, the expandable rounded members being expandable from a stored state to an expanded state and when in the expanded state each of the expandable rounded members are configured to expand to move into contact with the lumen in the organ, the lumen defining a longitudinal axis; and
wherein each of the expandable rounded members comprise a tissue tag, each of the tissue tags being magnetized or comprising a magnet;
wherein the expandable rounded members are configured to be located within and deployed from the insertion mechanism into the lumen in the organ at a predetermined location relative to the target tissue;

wherein the one or more tissue effecting elements are longitudinally movable relative to each of the expandable rounded members in a direction that extends along the longitudinal axis of the lumen; and an alarm system configured to provide a signal when the tip and the one or more markers are within a predetermined distance of each other;

wherein the one or more device tags present a magnetic field of common polarity respectively with each of the tissue tags of the device so that the one or more device tags provide an increase in tactile resistance to the tip of the one or more tissue effecting elements moving towards the tissue tags, the target tissue and the tissue tags are displaced as the one or more device tags are configured to be moved towards the target tissue and the tissue tags.

* * * * *